US008771930B2

(12) United States Patent
Curtis et al.

(10) Patent No.: US 8,771,930 B2
(45) Date of Patent: *Jul. 8, 2014

(54) EX VIVO METHODS FOR TESTING TOXICITY OF SUBSTANCES USING DONATED HUMAN ORGANS OR TISSUES

(75) Inventors: Gerald Curtis, Cardiff (GB); John Brassil, Northbrook, IL (US); David Kravitz, South Barrington, IL (US)

(73) Assignee: Lifeline Scientific, Inc., Des Plaines, IL (US)

( * ) Notice: Subject to any disclaimer, the term of this patent is extended or adjusted under 35 U.S.C. 154(b) by 756 days.

This patent is subject to a terminal disclaimer.

(21) Appl. No.: 11/802,059

(22) Filed: May 18, 2007

(65) Prior Publication Data

US 2008/0288399 A1     Nov. 20, 2008

(51) Int. Cl.
*A01N 1/00*     (2006.01)

(52) U.S. Cl.
USPC ............................................. 435/1.2; 435/1.1

(58) Field of Classification Search
CPC ....... A01N 1/02; A01N 1/247; G01N 33/574; G01N 33/68; G01N 33/566; G01N 33/5082; G01N 33/5014; G06Q 20/102; G06Q 50/22
See application file for complete search history.

(56) References Cited

U.S. PATENT DOCUMENTS

| | | | |
|---|---|---|---|
| 3,877,843 | A | 4/1975 | Fischel |
| 4,618,586 | A | 10/1986 | Walker |
| 4,629,686 | A | 12/1986 | Gruenberg |
| 4,666,425 | A | 5/1987 | Fleming |
| 5,051,352 | A | 9/1991 | Martindale et al. |
| 5,217,860 | A | 6/1993 | Fahy et al. |
| 5,328,821 | A | 7/1994 | Fisher et al. |
| 5,338,662 | A | 8/1994 | Sadri |
| 5,494,822 | A | 2/1996 | Sadri |
| 5,622,429 | A | 4/1997 | Heinze |
| 5,989,918 | A | 11/1999 | Dietz et al. |
| 6,023,630 | A | 2/2000 | Bacchi et al. |
| 6,024,698 | A | 2/2000 | Brasile |
| 6,046,046 | A | 4/2000 | Hassanein |
| 6,197,575 | B1 | 3/2001 | Griffith et al. |
| 6,582,953 | B2 | 6/2003 | Brasile |
| 6,592,567 | B1 | 7/2003 | Levin et al. |
| 6,673,594 | B1 | 1/2004 | Owen et al. |
| 6,699,231 | B1 | 3/2004 | Sterman et al. |
| 6,953,655 | B1 | 10/2005 | Hassanein et al. |
| 7,410,474 | B1 | 8/2008 | Friend et al. |
| 2002/0123141 | A1 | 9/2002 | Hariri |
| 2004/0002891 | A1 | 1/2004 | Chen et al. |
| 2004/0038193 | A1 | 2/2004 | Brasile |
| 2004/0224298 | A1 | 11/2004 | Brassil et al. |
| 2005/0015278 | A1 | 1/2005 | Ghouri |
| 2005/0255458 | A1 | 11/2005 | Polansky |
| 2005/0276792 | A1 | 12/2005 | Kaminski et al. |
| 2006/0019326 | A1 | 1/2006 | Vacanti et al. |
| 2007/0072222 | A1 | 3/2007 | Boess et al. |

FOREIGN PATENT DOCUMENTS

| | | |
|---|---|---|
| EP | 1 208 748 A1 | 8/2000 |
| JP | 2-258701 | 10/1990 |
| WO | WO 88/05261 A1 | 7/1988 |
| WO | WO 94/06292 | 3/1994 |
| WO | WO 95/31897 | 11/1995 |
| WO | WO 96/31779 | 10/1996 |
| WO | WO 98/09166 | 3/1998 |
| WO | WO 99/35245 | 7/1999 |
| WO | WO 99/45982 | 9/1999 |
| WO | WO 00/18226 | 4/2000 |
| WO | WO 02/026034 A2 | 4/2002 |
| WO | WO 2005/074681 A2 | 8/2005 |

OTHER PUBLICATIONS

Roediger W.E.W. et al. Effect of short-chain fatty acid on sodium absorption in isolated human colon perfused through the vascular bed. Digestive Diseases and sciences, Feb. 1981, vol. 26, No. 2, pp. 100-106.*
Desai T.R. et al. Defining the critical limit of oxygen extraction in the human small intestine, Journal of Vascular Surgery, 1996, vol. 23, No. 5, pp. 832-838.*
Bell Jr. R.H. et al. Ex-vivo isolated perfusion of the pancreas in the Syrian golden hamster, Internationational Journal of Pancreatology, 1 (1986), pp. 71-81.*
Coleman R.A. et al. Use of human tissue in ADME and safety profiling of development candidates, Drug Discosery Today (DDT), Nov. 2001, vol. 6, No. 21, pp. 1116-1126.*
tuberose.com—Environmental Toxicity, published online Feb $4^{th}$ 2005 on the web at http://tuberose.com/Environmental_Toxicity. html, pp. 1-8.*
Malgorzata Tokarska-Schlattner, et al. "Acute toxicity of doxorubicin on isolated perfused heart: response of kinases regulating energy supply," Am J Physiol Heart Circ Physiol, vol. 289, pp. H37-47, Mar. 11, 2005.
Jun. 28, 2011 Office Action issued in U.S. Appl. No. 11/598,800.
Feb. 10, 2011 European Search Report issued in GB0921330.7.
Mar. 25, 2011 European Search Report issued in GB0921349.7.
Dec. 21, 2011 Final Rejection issued in U.S. Appl. No. 11/598,800.
Mar. 17, 2010 Office Action issued in U.S. Appl. No. 10/845,154.
Feb. 3, 2011 Restriction Requirement issued in U.S. Appl. No. 11/598,800.

(Continued)

*Primary Examiner* — Satyendra Singh
(74) *Attorney, Agent, or Firm* — Oliff PLC

(57) ABSTRACT

Properties such as toxicity of substances may be determined by assaying properties, fates and effects of substances in an ex vivo metabolically active human organ or tissue under normothermic perfusion with a fluid containing a test substance. The data can be used as, for example, part of a submission to a government regulatory organization. Preferred methods use perfused endocrine gland organs or tissues to evaluate hormone or other bodily chemical disruption caused by substances and pre-donation diseased or injured organs or tissues.

23 Claims, No Drawings

(56) References Cited

OTHER PUBLICATIONS

Jan. 10, 2011 Final Office Action issued in U.S. Appl. No. 11/802,064.
Jul. 22, 2010 Office Action issued in U.S. Appl. No. 11/802,064.
Jan. 29, 2010 Election of Species Requirement issued in U.S. Appl. No. 11/802,064.
May 16, 2011 Office Action issued in U.S. Appl. No. 10/845,154.
Apr. 1, 2009 Office Action issued in U.S. Appl. No. 10/845,154.
Nov. 1, 2007 Office Action issued in U.S. Appl. No. 10/845,154.
Feb. 8, 2007 Office Action issued in U.S. Appl. No. 10/845,154.
Aug. 6, 2008 Office Action issued in U.S. Appl. No. 10/845,154.
Nov. 24, 2009 International Preliminary Report on Patentability issued in International Patent Application No. PCT/US2008/006369.
U.S. Appl. No. 10/845,154, filed May 14, 2004 to Brassil et al.
Sep. 6, 2011 European Office Action issued in EP 05 817 022.6.
Takahashi H. et al., "The Use of a Perfluorochemical Emulsion as a Vascular Perfusate in Drug Absorption", Journal of Pharmacy and Pharmacology, Pharmaceutical Press, vol. 40, No. 3, Apr. 1, 1988, pp. 252-257.
Svensson, U.S.H. et al., "High in situ rat intestinal permeability of artemisinin unaffected by multiple dosing and with no evidence of p-glycoprotein involvement," Drug Metabolism and Disposition, 1999, vol. 27, No. 2, pp. 227-232.
Jul. 29, 2008 International Search Report issued in PCT/US2008/006368.
Feb. 28, 2006 International Search Report issued in PCT/US2005/016057.
Oct. 18, 2011 United Kingdom Office Action issued in GB0921349.7.
Oct. 18, 2011 United Kingdom Office Action issued in GB0921330.7.
Dec. 5, 2011 Office Action issued in U.S. Appl. No. 10/845,154.
Dec. 7, 2011 Office Action issued in U.S. Appl. No. 11/802,064.
U.S. Appl. No. 11/598,800, filed Nov. 14, 2006, Brassil et al.
U.S. Appl. No. 11/802,064, filed May 18, 2007, Curtis et al.
"Human Data Before Human-Trials Improving Drug Discovery and Development Productivity with Ex Vivo Metrics," Katzenbach Partners LLC, 2005, pp. 1-22.
"Perfusion of the isolated rat liver," Curtis, C.G. et al., Proceedings of the Physiological Society, Dec. 1970, pp. 14P-15P.
"Degradation of [$^3$H]Chondroitin 4-Sulphate and Re-utilization of the [$^3$H]Hexosamine Component by the Isolated Perfused Rat Liver," Macnicholl, Alan D. et al., Biochem. J. (1980), vol. 186, pp. 279-286.
"Utilization by the Isolated Perfused Rat Liver of N-Acetyl-D-[1-$^{14}$C]galactosamine and N-[$^3$H]Acetyl D-galactosamine for the Biosynthesis of Glycoproteins," MacNicoll, Alan D. et al., Biochem. J.. (1978) vol. 174, pp. 421-426.
"NMR study of the whole rat bile: the biliary excretion of 4-cyano-N, N-dimethyl aniline by an isolated perfused rat live and a liver in situ," Ryan, David A. et al., Journal of Pharmaceutical & Biomedical Analysis, 1995, vol. 13, No. 6, pp. 735-745.
"Liver as major organ of phenol detoxication?," Powell, G. et al., Nature, Nov. 15, 1974, vol. 252, pp. 234-235.
"Oxidation of Sodium Sulphide by Rat Liver, Lungs and Kidney," Bartholomew, Terrence C. et al., Biochemical Pharmacology, 1980, vol. 29, pp. 2431-2437.
"The metabolic sulphation of polyethyleneglycols by isolated perfused rat and guinea-pig livers", Roy, A. B. and Maggs, J. et al., Xenobiotica, 1987, vol. 17, No. 6, pp. 725-732.
"Octan-2-sulphate degradation in the isolated perfused rat liver", Maggs, J. et al., Biochemical Pharmacology, 1984, vol. 33, No. 5, pp. 827-829.
*Isolated Perfused Liver Technology for Studying Metabolic and Toxicological Problems*, Powell, G.M. et al., 1989, vol. 7, No. 1, pp. 53-86.

"Organ Perfusion and Mass Spectrometry: A Timely Merger for Drug Development," Curtis, C. Gerald et al., Current Topics in Medicinal Chemistry, 2002, vol. 2, pp. 77-86.
"Predictive Models for Tissue Metabolism-Screening Using Organ Perfusion Methods," Curtis, G., CPSA Digest 2001, http://www.milestonedevelopment.com/CPSA/2001/day3oa3.html.
"Alterations of the renal function in the isolated perfused rat kidney system after in vivo and in vitro application of S-(1,2-dichlorovinyl)-L-cysteine and S-(2,2-dichlorovinyl)-L-cysteine," Ilinskaja, O. and Vamvakas, S., Arch Toxicol (1996), vol. 70, pp. 224-229.
A New Paradigm in Perfusion, http://res-del.com/resources/AQIX_RS-I.pdf, 2003.
"The Rate of Induction of Hypothermic Arrest Determines the Outcome in a Swine Model of Lethal Hemorrhage," Alam, H. et al., The Journal of Trauma Injury, Infection, and Critical Care, Nov. 2004, vol. 57, No. 5, pp. 961-969.
"Machine Perfusion of Isolated Kidney at 37° C. Using Pyridoxalated Hemoglobin-polyoxyethlene (PHP) Solution, UW Solution and Its Combination", T. Horiuchi et al., Biomaterials, Art. Cells & Immob. Biotech, vol. 20, Nos. 2-4,, pp. 549-555, 1992.
"In Situ Cadaver Kidney Perfusion", Robert T. Schweizer et al., Transplantation, vol. 32, No. 6, pp. 482-484, Dec. 1981.
"Intermediate Normothermic Perfusion During Cold Storage of Ischemically Injured Kidneys", J.G. Maessen et al., Transplantation Proceedings, vol. 21, No. 1, pp. 1252-1253, Feb. 1989.
"Perfusion of Rabbit Kidneys With Glycerol Solutions At 5° C.", D.E. Pegg et al., Cryobiology, vol. 14, pp. 168-178, 1977.
"Seleno-DL-Methionine Reduces Freezing Injury in Hearts Protected With Ethanediol", W.J. Armitage et al., Cryobiology, vol. 18, pp. 370-377, 1981.
"Banking of Cells, Tissues, and Organs At Low Temperatures", David E. Pegg, Current Trends in Cryobiology, Plenum Press, NY, pp. 153-180, 1970.
"Effect of Pharmacologic Agents on the Function of the Hypothermically Preserved Dog Kidney During Normothermic Reperfusion", Rutger J. Ploeg et al., Surgery, vol. 103, No. 6, pp. 676-682, Jun. 1988.
"Is Normothermic Preservation an Alternative to Hypothermic Preservation?", R. N. Dunn et al., Organ Preservation Basic and Applied Aspects, Chapter 38, pp. 273-277, 1982.
"Free Radicals and Myocardial Ischemia and Reperfusion Injury", Paul J. Simpson et al., J Lab Cin Med., pp. 13-30, Jul. 1987.
M.R. Buhl et al, "The Postanoxic Regeneration of 5'-Adenine Nucleotides in Rabbit Kidney Tissue during in Vitro Perfusion," 1976, pp. 175-181.
"Organko Servierungsmachine OKM 82", Von Dietmer Scholz et al., East German Article, 1983.
"MOX®-100 Renal Preservation System", Waters Instruments Medical Group, pp. 2-7, 1982.
"Organ Perfusion Systems: An Evaluation Criteria", Fereydoon Sadri, Ph.D., T.O.P.S. Medical Corporation, pp. 1-8, 1987.
D.K. Hansen et al., "Pharmacokinetic and Metabolism Studies Using Microdialysis Sampling," J. Pharmaceutical. Sciences, Jan. 1999, vol. 88, No. 1, pp. 14-27.
G. Nowak et al., "Metabolic Changes in the Liver Graft Monitored Continuously With Microdialysis During Liver Transplantation in a Pig Model," Liver Transplantation, May 2002, vol. 8, No. 5, pp. 424-432.
S.C. Baicu et al., "Interstitial Fluid Analysis for Assessment of Organ Function," Clin. Transplant, Jun. 24, 2004, vol. 18, No. 12, pp. 16-21.
Sep. 26, 2013 Office Action issued in Chinese Patent Application No. 2013092300947840 (with translation).
Oct. 23, 2013 Office Action issued in U.S. Appl. No. 11/598,800.
May 22, 2012 Office Action issued in U.S. Appl. No. 11/802,064.
Mar. 28, 2013 Chinese Office Action issued in Chinese Patent Application No. 200880024743.5 (with translation).

* cited by examiner

EX VIVO METHODS FOR TESTING TOXICITY OF SUBSTANCES USING DONATED HUMAN ORGANS OR TISSUES

BACKGROUND

The disclosure relates to using perfused human-derived organs and/or tissues, such as glandular organs and/or tissues, to evaluate hormone, or other bodily chemical, disruption caused by substances. Methods of the invention permit assessment of such substances using human organs and/or tissues, particularly organs unsuitable for transplantation, on an organ-by-organ or tissue-by-tissue basis.

Methodologies available for assessing properties, fates and effects of substances in humans span many levels of mammalian organization from in vivo studies to studies of isolated organs or tissues, tissue slices, cultured cell types, subcellular particles, multi-enzyme complexes and molecular interactions. In practice, these complex methods often result in considerable wasted time, effort and resources in many fields where substances may undergo several rounds of testing only to find that later testing or market experience reveals undesirable effects in humans, often with tragic consequences.

Historically, attempts to weed-out substances having an unacceptable benefit/risk ratio have relied on in vivo non-human animal studies using several species, such as rodent species. Limitations of toxicity studies in non-human species have long been, and still are, well recognized, but short of performing toxicity studies in humans in vivo there has been no viable alternative. Attempts have been made to bridge the gap between non-human testing and human effects using tissue preparations including subcellular particles, e.g., microsomes, primary cells and cells in culture, e.g., hepatocytes, and tissue slices. Although these in vitro tissue preparations generate much useful data, the farther the tissue preparation is from the whole organism, the greater the risk of false positives and false negatives. For example, false positives or false negatives may occur when assessing whether test substances are toxic when administered alone or with other co-administered substances. Moreover, there is no guarantee that pharmacokinetic/toxicity relationships in normal human tissues determined in vitro will be the same as in normal or diseased human tissues in vivo.

As it is not ethical to use humans for exploratory toxicity testing, the choice has been to perform in vivo testing on a variety of non-human animal species and/or in vitro testing using human biological samples. For example, drug testing using ex vivo human organs has been disclosed in the present assignee's published PCT Application No. WO 2005/074681 and U.S. patent application Ser. No. 10/768,167 (the entire contents of which are hereby incorporated by reference in their entirety), which notes that organs unsuitable for transplantation may be used for such testing.

Studies have shown that human reproductive health may be linked to environmental substances that have oestrogenic, androgenic or related potentials. A number of observations have been made from human epidemiological studies that include reduced sperm counts, reduced fertility, increased incidence of testicular cancer and congenital birth defects in men and increased incidence of breast cancer in women possibly due to environmental substances. In various wildlife species, the occurrence of gross birth deformities, behavioral abnormalities and feminization/masculinization have been reported. Clearly, many concerns exist that such substances may adversely affect human reproductive health and other aspects of human well-being. See, e.g., *Draft Detailed Review Paper: Appraisal of Test Methods for Sex-Hormone Disrupting Chemicals*, from the *Series on Testing and Assessment*, OECD Environmental Health and Safety Publications, Environment Directorate, Organisation for Economic Co-operation and Development, Paris, France (1997).

SUMMARY

As noted above, current testing methods, while beneficial, are not fully competent for identifying compounds that are toxic or have other deleterious effects in humans. The present disclosure provides improved methods for evaluating effects of substances on humans that bridge the gap between effects obtained from in vivo non-human animal testing and actual effects in humans. The present disclosure also provides standardized, cost-effective screening tests to evaluate the human hormone-disrupting and other bodily chemical-disrupting potential, e.g., increasing, decreasing or otherwise altering, hormone or other bodily chemical levels, of substances, or affecting hormone production or uptake. The present disclosure also provides for more direct testing of substances, including drugs and drug candidates, than known "models" for such testing. For example, rather than using healthy organs that may be modified or treated to provide disease or injury "models," the present disclosure provides methods using actual organs and tissues that were subject to pre-donation disease or injury for testing effects of substances, including efficacy and/or safety of the substances in connection with such organs or tissues.

Methods provided herein reduce the chance of unforeseen human morbidity and mortality related to certain substances. Resulting data showing fates and effects of substances in perfused human organs and/or tissues are more reliable and clinically relevant than data from in vitro systems that lack a blood supply and full complement of integrated cell types or from in vivo non-human animal models. Embodiments include ex vivo perfusing human organs and/or tissues, more preferably human organs, most preferably human organs unsuitable for transplantation, including diseased or injured organs or organs otherwise having a lower than acceptable likelihood of successful transplantation (which may be determined before or after donation and/or storage) due to, inter alia, prolonged warm ischemia times, disease, injury and/or prolonged storage, with a perfusate comprising at least one substance for assessment, as well as methods for identifying physiological effects of the substance. Preferably, the organ or tissue is a human organ or tissue, including glandular organs or tissues such as liver, lung, kidney, intestine, heart, pancreas, spleen, testes, placenta, thymus, arteries, veins, lymph nodes, bone or skeletal muscle, male or female reproduction organs, or endocrine/exocrine glands, including, for example, adrenal glands.

The organ or tissue may be a metabolically active human organ or tissue that has been permanently removed from its origin, or an engineered organ or tissue derived from isolated and/or cultured human cells, wherein the isolated and/or cultured human cells may comprise stem cells (collectively referred to herein as "human organ(s) or tissue(s)" except where otherwise specified).

Embodiments provide methods of determining the fates and effects of substances, such as a chemical compound, in ex vivo perfused human-derived organs and/or tissues with respect to, for example, absorption, transport, metabolism, elimination, efficacy and/or toxicity of the substance, and, more specifically: rate and extent of substance absorption; extraction; identification of metabolites; organ control of the concentration of the substance and/or metabolites in plasma; tissue binding and accumulation; and tissue clearance and elimination.

In embodiments of the invention, methods can be applied to testing substances using perfused human organs or tissues, especially glandular organs or tissues, to evaluate hormone, or other bodily chemical, disruption caused by the substances. Substances include, but are not limited to, drug candidates, pharmaceuticals, and also non-drug- or pharmaceutical-related substances.

In embodiments, methods are provided of determining the fates and effects of a test substance on at least one human organ or tissue, comprising:

a) perfusing at least one human organ or tissue with a medical fluid to preserve said organ or tissue in the presence and absence of at least one test substance; and b) analyzing the organ, tissue, perfusate and/or downstream organs and/or tissues to detect the fates and effects of the test substance in the organ or tissue.

In embodiments, the analysis comprises comparing the organ or tissue in the presence and in the absence of the test substance.

In embodiments, the fates and effects of the test substance may be detected morphologically or histochemically, preferably, immunohistochemically, by analyzing biopsy samples and detecting changes or lesions therein.

In embodiments, the fates and effects of the test substance may be detected biochemically by assaying for toxic metabolites or end-products or for the liberation into the perfusate of intracellular molecules, such as enzymes, for example, lactate dehydrogenase, that are indicative of effects of the test substance, particularly toxicity.

In embodiments, fates and effects of the test substance may be detected by changes in gene expression in cells comprising the perfused organ or tissue by, for example, in situ hybridization with a probe that specifically hybridizes to at least one mRNA-encoded gene expressed by the organ or tissue. Assays for cell death, particularly apoptosis and necrosis, indicative of future toxic effect, may be performed.

In embodiments, fates and effects of the test substance may be detected by assaying an effluent from the perfused organ or tissue. Preferably, the perfusion effluent is a functional effluent depending on the organ or tissue, such as kidney urine, liver bile or lung mucus or an effluent comprising pancreatic exocrine digestive enzymes. Secretory products such as hormones released into perfusion effluent, and/or their effects or downstream target tissues or cells may be assayed. In embodiments, the effluent may be assayed after it is recovered leaving the organ or tissue via a vein, such as insulin and glucagons from the pancreas, albumin and glucose from the liver, oxygen and carbon dioxide from the lung or creatinine from the kidney. In the heart and intestine, effects of a test substance, particularly toxic effects, may be detected by a motor response, such as heartbeat and peristalsis. Additionally, absorption, transport, metabolism, elimination, efficacy and/or toxicity may be detected in any organ or tissue by changes in vascular resistance, and, specifically with regard to toxicity testing in the lungs, by changes in respiratory compliance.

Analysis may also, or alternatively, comprise electrophysiological testing, medical diagnostic imaging, spectroscopic testing, microdialysis, solid state tissue probe testing or a combination thereof.

Preferably, the organ or tissue is perfused under physiological temperature, pressure, oxygenation, osmolality, electrolyte balance and pH. In embodiments, the perfusate comprises matched human erythrocytes in a physiologically-acceptable medical fluid. The medical fluid advantageously further comprises about 2 to about 6% human serum albumin, N-acetylcysteine, adenosine monophosphate (AMP) and/or superoxide dismutase. In certain organs, such as the heart and liver, nervous stimulation may be provided as well during perfusion. In embodiments, wherein the organ is a liver, the medical fluid may comprise secretin or bile acids. In embodiments, wherein the organ is a kidney, the medical fluid may comprise a mixture of essential and non-essential amino acids. In embodiments wherein the organ is intestine, the medical fluid may comprise dexamethasone or noradrenaline.

In embodiments, the organ or tissue is perfused with a first medical fluid that does not comprise a test substance, followed by perfusion with a second medical fluid comprising a test substance. The medical fluids can be the same (but for the presence of the test substance) or different or adapted to identify the fates and effects of the test substance.

Methods provided by the invention advantageously avoid the inherent species differences in testing substances encountered when using non-human animal models to mimic in vivo activity and behavior in humans. In addition, perfused human organs or tissues can be exposed to substances under physiological conditions and at relevant concentrations to all cell types in the organ or tissue, or even in an entire or partial organ system, thereby providing more reliable, accurate and consistent results. In ex vivo testing, all cell types are in their normal proportions and orientations with respect to blood and tissue. Thus, test substances can be delivered as they would be in vivo, wherein the cell types retain their phenotype in the whole organ or tissue.

Thus, methods of the invention provide improved access to information and substance/effect correlations, because the information is obtained from ex vivo tests using perfused human-derived organs or tissues rather than from in vitro testing or in vivo non-human animal studies. Moreover, the resulting information can be further validated by assessing the suitability of the organ or tissue for substance testing as described in simultaneously filed co-pending U.S. patent application Ser. No. 11/802,064, the entire contents of which are incorporated herein by reference in their entirety.

Embodiments of the present invention include methods for evaluating a substance comprising passing a substance to be evaluated through a metabolically active ex vivo human organ or tissue, collecting data from the organ or tissue, perfusate and/or effluent, and/or downstream organ and/or tissue, and using the collected data to evaluate the fates and effects of the substance on the organ or tissue.

In embodiments, the evaluation method comprises passing a second substance through the organ or tissue before, simultaneously with or after the first substance and collecting data on the interaction of the first and second substances.

In embodiments, the evaluation method comprises perfusing the organ or tissue with a first fluid that does not contain the substance and then with a second fluid that contains the substance. Preferably, the second fluid is otherwise identical to the first fluid.

Embodiments of the invention include methods of collecting data as part of a governmental regulatory approval process comprising: providing an isolated metabolically active ex vivo human organ or tissue; perfusing through the organ or tissue a perfusate containing a test substance to be evaluated; collecting data from the perfusate, effluent and/or organ or tissue; and using data collected as part of a submission to a governmental regulatory organization.

Embodiments of the invention include methods of generating revenue comprising charging a fee to a third party for conducting testing to assess the fates and effects of a substance and, once the data is collected as described herein, providing the data to the third party.

In methods of generating revenue, data can be provided in raw form or analyzed before it is provided to the third party. The data can be used as part of a governmental and/or regulatory submission. The data can be owned by the party performing the testing and, optionally, the analysis, or the party requesting the evaluation. The fee may be a lump sum payment or other alternative.

In embodiments, the method of collecting data may comprise using the data as part of a process to resolve conflicting data across species, assess a substance's toxicity, determine the presence of metabolites, assess a substance's bioavailability, absorption, therapeutic effects and/or drug, or other chemical, interactions, and/or evaluate human hormone-disrupting and/or other bodily chemical-disrupting potential, e.g., increasing, decreasing or otherwise altering, hormone and/or other bodily chemical levels, of substances.

Embodiments of the invention provide information products. Such information products may comprise data relating to data generated, at least in part, by perfusing a substance through an ex vivo metabolically active human organ or tissue. In embodiments, the information product is provided in a computer-readable form.

Additional features and advantages of the present invention are described in, and will be apparent from, the following detailed description of embodiments.

DETAILED DESCRIPTION OF EMBODIMENTS

Embodiments of the invention include methods for using organs and/or tissues, preferably, human-derived organs and/or tissues, more preferably, human organs, to determine the fates and effects of a substance on the organs and/or tissues. Preferably, the organ or tissue is a human organ or tissue, such as liver, lung, kidney, intestine, heart, pancreas, spleen, testes, placenta, thymus, arteries, veins, lymph nodes, bone or skeletal muscle, or glandular organ or tissue, such as endocrine/exocrine glands, including, for example, adrenal glands, thyroid glands, and male and female reproductive organs.

As used herein, the terms "absorption," "transport," "metabolism" and "elimination" are understood to apply to any organ or tissue employed, but are specifically relevant to certain tissues and organs used in perfusion-based testing. For example, absorption is particularly relevant to the intestines and lungs; whereas transport, such as plasma clearance and metabolism, although also relevant to the intestines and lungs, is particularly relevant to the liver, kidneys and heart. Elimination is particularly relevant to the intestines, liver, kidneys and lungs.

As used herein, the term "toxicity" encompasses physical, chemical, biochemical and biological damage to organ or tissue, including at the cellular level. Toxicity is related to deleterious or other effects of substances on tissues and organs, including, but not limited to cell death, apoptosis, genetic mutation, changes in gene expression, biochemical inhibition, reductions in metabolism, induction and oxidative damage, as well as deleterious effects resulting from drug interactions. The term "toxicity" includes, but is not limited to, hormone disruption or other bodily chemical disruption. The term "disruption" includes, but is not limited to, increasing, decreasing or otherwise altering the level of hormones or other bodily chemicals that are in the blood or other bodily fluid or that are secreted, and/or altering the ability of target tissues or cells to respond to hormones or other bodily chemicals. For example, altering receptor-mediated or other potential interactions is included within the term description.

The term "efficacy" encompasses a measure of the positive, homeostatic or health-promoting effects of a test substances on a organ or tissue. Such measures include, but are not limited to, assays for reducing or eliminating disease-specific biomarkers, preferably using diseased organs or organs otherwise infected by a pathogen.

In certain embodiments, methods of the invention include detecting tissue- or organ-specific biomarkers for acute or chronic toxicity induced by a test substance. The biomarker may be, for example, a pathogen-associated marker of either pathogen or cellular origin or a metabolic breakdown product. Organs or tissues that were injured or diseased before donation may be particularly useful in methods of the invention. For example, an organ from a donor that had a disease that a drug candidate is intended to treat can be particularly useful in drug development. Organs and tissues of this type include those subject to bacterial and/or viral infection, inflammation and/or tumors, diabetic organs or tissues, and organs that have been subjected to pre-donation impact trauma. For lungs or lung tissue, such pre-donation conditions may include asthma, chronic obstructive pulmonary disorder, and cystic fibrosis; for hearts or heart tissue, they may include arrhythmia; for livers and liver tissue, they may include cholestasis, jaundice, portal hypertension, necrosis, and cirrhosis; for kidneys or kidney tissue, they may include acute renal failure; for pancreases or pancreas tissue, they may include pancreatitis.

As provided herein, methods of determining the fates and effects of a substance on a organ or tissue comprise: contacting a organ or tissue with a substance by perfusion of the organ or tissue with a medical fluid containing the substance. The terms "substance," "test substance," "test compound," and "compound" are used interchangeably and except as otherwise specified include, but are not limited to, drug- or pharmaceutical-related substances such as drug candidates and pharmaceuticals and also non-drug- or pharmaceutical-related substances such as environmental substances, such as smoke and other industrial effluents; agricultural products and by-products; building materials; manufacturing products and by-products; food products such as food processing products and by-products, foods and food additives; tobacco products such as cigarette, cigar or pipe smoke or chewing tobacco extracts and components thereof; cleaning products such as detergents, bleaches, soaps, shampoos and conditioners; cosmetics such as skin, hair and nail cosmetics; etc.

Perfusion preservation is applied routinely to organs for clinical transplant, wherein perfusion at hypothermic arrest (about 4° C. to about 8° C.) is the preferred method of preservation. In contrast, organ preservation for transplant under physiologic conditions, including normal body temperature (normothermia), although studied at length, has not been clinically applied because it is difficult in practical applications to maintain an organ at normal body temperature. To some extent, the application of normothermia has been limited by the high demands placed on a transplanted organ, specifically that it be both maximally functional and minimally inflammatory. Because demands of transplantation are reduced or non-existent in the ex vivo methods of the invention, many of the limitations of normothermia are overcome. For example, ex vivo normothermic organs may be supplied with oxygen via type-matched blood cells without concerns of immunogenicity, and may acceptably experience degraded functionality during normothermic perfusion, e.g., as toxins normally cleared by other organs accumulate and as substrates and factors normally produced by other organs are depleted. As used herein, "normothermic conditions" refers to temperatures in the range of 37±3° C.

Embodiments include business methods and models of using features of the present invention to provide improved access to substance information, such as, for example, substance/effect correlations. Thus, embodiments may include making available to a third party a service including conducting testing of the fates and effects of a substance on human organs or tissues. Specific embodiments include making available to a third party the resulting data and/or information generated from the testing in the form of an information product. The service and product may be made available to a third party for a fee. It should be appreciated that a fee may include a fixed amount or lump sum, an amount that is based on a variable or any other suitable form of remuneration, compensation or reimbursement.

Accordingly, an entity that conducts testing according to the disclosed methods and generates data and information from the disclosed methods, referred to herein as a provider, may generate revenue from marketing and selling services and products described herein to third parties.

Additional embodiments include a preservation stage in which one or more organs or tissues derived from a target species, such as a human, are preserved under hypothermic conditions such that the organs or tissues maintain the capacity to resume and sustain substantially normal metabolic activity and function upon return to physiologic temperature. As used herein, the term "metabolically active" refers to a level of biochemical activity characteristic of a living organism.

In a functional stage, organs or tissues may be perfused with a normothermic blood or blood-based perfusate to stabilize the organ or tissue physiology. The physiology and biochemistry of the organ or tissue is preferably maintained substantially in accordance with the physiology and biochemistry of an organ or tissue in vivo, such that data generated from the testing is substantially unequivocal, reproducible and relevant. In whole organs, for example, cells retain their phenotypes, cell types are present in their normal proportions and orientations with respect to blood and tissue, and substances have the effects that they would in vivo.

The functional state of test organs or tissues may be quantified by the inclusion of positive and negative controls. The control(s) may be added either before or simultaneously with the substance or after substantially all the essential samples required for analysis of the fates and effects of the substance have been collected. A fluid or perfusate that does not contain the substance may be passed through the organ before and/or after perfusing the organ or tissue with a second fluid that contains the substance. In this way, the organ may act as its own control. The positive and/or negative controls used depend on the primary objective of the particular test.

Embodiments of methods may be conducted in "normal," "diseased" or injured organs and tissues, wherein the physiology and biochemistry of each organ or tissue is maintained as close as possible to in vivo characteristics and properties for that particular disease or condition. Embodiments of methods may comprise use of multiple medical devices, solutions and protocols, including sourcing, procuring, preserving and evaluating research organs and/or tissues.

In aspects, the disclosed methods may generate data and information about a substance and its fates and effects with respect to human organs and/or tissues. Data or information about the substance may include characteristics of the substance itself, its derivatives, metabolites and/or related substances.

Data or information obtained about the substance may include the effects of the substance on ex vivo organs or tissues, the effects of ex vivo organs or tissues on the substance and the effects of the substance on other substances exposed or related to the ex vivo organs or tissues or their products. Information about the substance and its fates and effects may include, but is not limited to, absorption, transport, metabolism, elimination, efficacy and/or toxicity of the substance, and, more specifically: rate and extent of substance absorption; extraction; identification of metabolites; organ control of the concentration of the substance and/or metabolites in plasma; tissue binding and accumulation; and tissue clearance and elimination. Information may further include assessments of the human hormone-disrupting and other bodily chemical-disrupting potential, e.g., increasing, decreasing or otherwise altering, hormone or other bodily chemical levels, of substances.

In another aspect, disclosed methods may generate data and information about the ex vivo organ or tissue exposed to the substance. In applications of disclosed methods, testing results may provide data and information on classes of substances, cellular receptors, biochemical pathways, physiological and pathological mechanisms, biomarkers and other phenomena associated with living organisms. Accumulated data and information generated in performing disclosed methods may create a resource of statistically significant and scientifically valid information. Each of these forms of data and information may constitute a transferable information product.

In embodiments, an information product provided to a third party may include raw data generated from performing disclosed methods. Alternatively, or in addition, an information product provided to a third party may include an interpretation or evaluation of raw data in various levels of useful and/or conclusory forms. Raw data may be retained as proprietary by the provider, and only information derived from the raw data may be made available as an information product to the third party. Therefore, in addition to the service of conducting the testing according to disclosed methods and generating raw data, a provider may interpret data for a third party.

Information products may be in the form of access to this resource of information made available to a third party for a fee. Such information may be used to, for example, compare effects in various types of tissues and organs to formulate patterns and models of predictability of those effects. Information products may be used to compare information about the substance and its fates and effects in different tissues and organs, in different species and under different conditions of tissues and organs such as normal, abnormal, diseased or injured or otherwise damaged tissues and organs.

EXAMPLES

The nature of the perfusate is preferably adapted to the particular tissue, organ or combination thereof to be tested, or to the chemical or other characteristics of the test compound. For perfusion under hypothermic conditions, the perfusate preferably comprises: calcium chloride, sodium hydroxide, HEPES or other organic acids, phosphate (inorganic or organic ester), mannitol, glucose, sodium gluconate, magnesium gluconate, ribose, starch, glutathione, adenine and water.

A preferred perfusate used in hypothermic conditions, such as KPS-1® (Organ Recovery Systems, Inc., Des Plaines, Ill.), has a pH of about 7.4 and an osmolality of about 330 mOsm and comprises the following components:

| Component | Amount (g/1000 ml) | Concentration (mM) |
|---|---|---|
| Calcium chloride (dehydrate) (ionized) | 0.068 | 0.5 |
| Sodium hydroxide | 0.70 | 18 |
| HEPES (free organic acid) | 2.38 | 10 |
| Potassium phosphate (monobasic) | 3.4 | 25 |
| Mannitol (USP) | 5.4 | 30 |
| Glucose, beta D (+) | 1.80 | 10 |
| Sodium gluconate | 17.45 | 80 |
| Magnesium gluconate D (−) gluconic acid, hemimagnesium salt | 1.13 | 5 |
| Ribose, D (−) | 0.75 | 5 |
| Hydroxyethyl starch (HES) | 50.0 | n/a |
| Glutathione (reduced form) | 0.92 | 3 |
| Adenine (free base) | 0.68 | 5 |
| Sterile water | to 1000 ml volume | n/a |

For perfusions under normothermic conditions, the perfusate preferably comprises: water, sodium, potassium, calcium, magnesium, chloride, buffer component (containing bicarbonate ions and TES, MOPS or BES, for example), glucose, glycerol, choline, amino acid component (such as glutamate, aspartate and/or glutamine), co-enzyme (such as thiamine cocarboxylase), vitaminoid (such as carnitine) and protein (such as insulin). Alternatively, human blood plasma can be used.

A preferred perfusate used in normothermic conditions, such as RS1 (AQIX®, London, England) or OPB-1 or OPB-2 (Organ Recovery Systems, Inc., Des Plaines, Ill.), has a pH ranging from about 7.13 to about 7.41 and an osmolality of about 286 mOsm and comprises the following components:

| OPB-1 Components | OPB-1 Concentrations (mM) |
|---|---|
| Organic acids | 5 |
| Chloride | 116.4 |
| Sodium | 135 |
| Calcium (ionized) | 1.2 |
| Potassium | 5 |
| Bicarbonate ions | 25 |
| Glucose | 10 |
| TPP (cocarboxylase) | 0.04 |
| Magnesium (ionized) | 0.45 |
| Glutamine | 0.4 |
| Glutamate | 0.3 |
| Glycerol | 0.11 |
| Carnitine | 0.05 |
| Sterile water | n/a |
| Aspartate | 0.02 |
| Choline | 0.01 |
| Protein (Insulin) | 0.002 (25.00 mIU) |
| Bovine serum albumin | 6% |
| Buffer (BES) | n/a |

Additionally, perfusates can be modified for use with certain organs, as described in the following table by way of example.

| Organ | Chemical | Amount Range | Preferred Amount |
|---|---|---|---|
| Liver | N-acetylcysteine | 37-150 mg/l | 75 mg/l |
|  | ATP | 5-20 mg/l | 10 mg/l |
|  | Dibutylcyclic AMP | 12-50 µM | 25 µM |
|  | Superoxide dismutase | 1-4 µg (in 5% acid) | 2 µg (in 5% acid) |
|  | Glycocholic acid | 50-200 µM | 100 µM |
|  | Glycochenodeoxycholic acid | 25-100 µM | 50 µM |
|  | $^3$H-mannitol | 50-200 µg (if required) | 100 µg (if required) |
| Intestine | Noradrenaline | 1-5 µl/l | 2.25 µl/l |
|  | Dexamethasone | 1-4.5 ml/l | 2.2 ml/l |
| Kidney | Methionine | 37-150 mg/l | 74.6 mg/l |
|  | Alanine | 89-160 mg/l | 178.2 mg/l |
|  | Glycine | 75-300 mg/l | 150.1 mg/l |
|  | Serine | 105-420 mg/l | 210.2 mg/l |
|  | Proline | 115-260 mg/l | 230.2 mg/l |
|  | Isoleucine | 65-262 mg/l | 131.2 mg/l |
|  | Mannitol | 0.5-2 g/l | 1 g/l |
|  | Creatinine | 7-27 mg/l | 14.61 mg/l |
|  | N-acetylcysteine | 0.35-1.4 g/l | 0.7 g/l |
|  | ATP | 0.01-0.06 g/l | 0.03 g/l |
|  | Dibutylcyclic AMP | 0.01-0.06 g/l | 0.03 g/l |

Perfusion Study Reports

If a report of the perfusion study results is to be provided to a third party or simply retained, the report can be in draft or final form and contain study information and data including, but not limited to: description of the experimental procedures including, for example, the perfusion method and preparation details; organ or tissue weight at the start and end of the perfusion study; mass balance data of, for example, radioisotopes in perfusate, plasma, effluent, organ or tissue, and/or bodily fluids, such as bile, as applicable; plasma and/or organ or tissue clearance of standards (also termed "controls"), control methodologies and substances; excretion of conjugated and unconjugated standards and any applicable conjugates; rate of formation of metabolites of standards and other facets of the metabolic profiles of standards; description of standards, including, for example, metabolic profiles; physiological flow rates at each collection timepoint, e.g., bile, arterial, etc., as applicable; organ donor details and medical records (as permitted); test substance data sheets or other available information; test substance receipts and usage records; dosing records; sample collection records; sample weight records; sample storage and shipment records; location of study site; any additional measurements and/or analyses performed during the study or otherwise related to the study; and/or any reports and/or data supplied by a contract facility.

Hormone or Other Bodily Chemical Disruption

When assessing the toxicity or other effect(s) of a substance on hormones or other bodily chemicals, useful information includes, but is not limited to, determining how a substance affects the ability of exocrine/endocrine or other glands to produce and/or respond to effector hormones in the blood and other bodily fluids and at what concentration, e.g., is the hormone or other chemical level unaltered, decreased, increased or otherwise altered or is the secretion ability of the exocrine/endocrine or other glands unaltered or altered. Additionally or alternatively, it may be useful to determine how a substance affects the ability of target cells or tissues to respond to hormones or other bodily chemicals produced by endocrine/exocrine or other glands, e.g., receptor-mediated or other potential reactions.

The preferred test system for hormone and other bodily chemical disruption testing is one in which the blood supply to and from the exocrine/endocrine or other glands and the target tissue(s) is intact. The test substance is preferably delivered to the exocrine/endocrine or other gland under controlled conditions such that the secretory products normally released by the exocrine/endocrine or other gland into the blood, or other bodily fluid, in response to hormones, or other bodily chemicals, can be evaluated. Preferred organ models include, but are not limited to, pancreas, thymus, male and female reproductive organs, thyroid gland and adrenal gland.

The mechanisms of action of substances suspected of affecting one or more aspects of endocrine function, including, but not limited to, reproductive, adrenal and thyroid function, can involve multiple sites of action and complex disturbances in the homeostatic processes, such as disruption of endocrine, or other system, secretion, binding, feedback-control and/or target activity. Indirect effects include, but are not limited to, those that result from a substance inducing or inhibiting metabolic enzymes and causing changes in the production or breakdown of endogenous hormones or other bodily chemicals or causing alterations in carrier protein levels in the blood or other bodily fluid.

For example, sex hormone disrupters and their metabolites may, if structurally similar to endogenous ligands, interact directly with the physiological ligand's receptor in the cells of the gonads or accessory sex organs, thus either mimicking the action of the hormone resulting in receptor stimulation or other agonistic effect, or resulting in blocking or reducing the binding and biological activity of naturally present hormones or other antagonistic effect.

Set forth below are assays and organs or tissues illustrating methods of the invention. This disclosure is of a general nature and the non-limiting protocols below merely provide embodiments of the general disclosure.

Perfused Intestine Protocol Example

The ability to generate unequivocal data regarding the absorption of substances in the human intestine, prior to clinical trials, is important in decisions regarding the use of substances that might be ingested. Such data can be generated using isolated intestinal segments because: (a) the substances are presented via the intestinal lumen as in vivo; (b) the barriers between the intestinal lumen and blood are present and intact; and (c) the composition and flow characteristics of the perfusate mimic those in vivo.

Perfusion Conditions

Approximately three liters of perfusate are used per analysis. The perfusate preferably comprises matched human erythrocytes (preferably, previously washed) suspended in a buffer (at about 15 to about 20% (v/v)) comprising 4-6% human serum albumin, at a pH of preferably about 7.4.

Preferably, the perfusate is passed through a blood transfusion filter, followed by a leukocyte-removing filter, heparin is added and the pH adjusted, if necessary, to, preferably, about 7.4. The perfusate is preferably stored at room temperature until added to the perfusion apparatus. An aliquot of the surplus perfusate can be centrifuged (at about 1500 g for approximately 10 minutes at approximately 4° C.) to separate the plasma. The plasma can then be frozen at approximately −20° C. or lower for use as blanks in the analysis.

Intestine Samples and Perfusion

Isolated segments (about 30 cm to about 45 cm) of human intestine, immediately below the entry of the bile duct, for example, are preferably removed from hypothermic storage and used for each analysis.

The entire intestine sample is weighed and flushed with cold buffer via the mesenteric artery (or a branch thereof) for about 10 to about 15 minutes, at approximately 4-8° C., at a pH of approximately 7.4 and at a pressure of approximately 60-80 mmHg. This arterial buffer flush generally involves about 0.5 liter of buffer.

Following the arterial buffer flush is the equilibration period, wherein about 0.5 liter of oxygenated room temperature perfusate is passed through the intestine at a rate of approximately 20 ml/min. Approximately 0.5 liter of perfusate effluent is allowed to run to waste and the perfusion then switched to recirculating mode with 0.75 liter of oxygenated perfusate. The perfusion flow rate is preferably increased up to a target of about 90 to about 100 ml/min. over time without exceeding maximum pressure limits. The perfusate is recirculated until the intestinal core temperature is greater than about 35° C. and peristalsis is visible. The first pass and first recirculation combined generally last up to about 60 minutes.

At the end of the equilibration period, the perfusate is drained from the apparatus and replaced with about one liter of fresh oxygenated perfusate at about 37° C. in recirculation mode. This period is the stabilization period, which lasts for about 10 to about 15 minutes. Subsequently, perfusate aliquots are removed provided perfusion and physiological parameters, e.g., oxygen uptake, core temperature more than about 35° C., flow of about 90 ml/min. and pressure between about 60 to about 80 mmHg, are satisfied.

Dosing and Sample Collection

Preferred acceptance criteria for normothermic perfusion of human intestine prior to dosing with a test substance are:

| Perfusion & Physiological Parameters | |
|---|---|
| Arterial pressure (mmHg) | 100 |
| Arterial flow (ml/min./gram) | 0.2-1.0 |
| Venous $PO_2$ | >26 |
| Arterial $PO_2$ | >120 |
| pH | 7.3 ± 0.2 |
| Temperature (° C.) | 37.4 ± 2 |
| PCV (% cells) | 20-45% |

The preferably labeled, e.g., radiolabeled, test substance (approximately 10 mg, approximately 100 µCi) and preferably 3-5 labeled internal standards, which are absorbed by passive diffusion at different rates, are administered, preferably as a pulse dose, in the same formulation in a maximum volume of about 15 ml into the lumen of the isolated intestine. This is designated "time zero."

The intestine is then perfused, in recirculating mode, preferably for about 2 hours and aliquots (about 3 to about 5 ml) of the perfusate are removed, preferably at least two of the following preferred times: pre-dosing and 5, 10, 15, 30, 45, 60, 90, 105 and 120 minutes post-dosing. Approximately half of each sample is frozen at about −70° C. and the remainder of each sample is centrifuged and the plasma removed and frozen at about −70° C. Alternatively, in five milliliter samples, for example, about 1 milliliter is retained as whole perfusate and the remaining about 4 milliliters centrifuged and the plasma supernatant divided into four approximately equal aliquots for separate analyses.

At termination of the perfusion, the intestinal segments are weighed, lumen contents are collected and weighed, and the lumen is flushed with about 100 milliliters of water and added to the intestinal contents and the combined mass recorded. The mixture is homogenized in a minimum amount of water and frozen for subsequent analysis, if desired, in approximately equal aliquots, such as about 40 milliliter aliquots. In addition, the perfusion apparatus is preferably rinsed with saline, water and/or alcohol. A sample of each rinse can be retained for subsequent analysis (e.g., mass balance).

Embodiments of the perfusion method allow for multiple (single or cassette) dosing into sequential segments of the same intestine. In such embodiments, the entire intestinal segment is perfused, as above, but after equilibration, the intestine (mesentery and lumen) is separated into three segments, preferably of approximately equal length, such that the lumen of each of the three segments is entirely separate, although the perfusate still circulates through each segment and subsequently mixes. One of the segments is then dosed with test substance and standards and aliquots of perfusate removed at timed intervals up to about one hour to about two hours post-dosing. This segment is then removed adjacent to the mesentery by, for example, cauterization, leaving the mesentery intact, but sealed. A liter of fresh perfusate is then flushed through the two remaining segments and the eluent collected in the first pass. Fresh perfusate (about 1 liter to about 1.5 liters) is then added and recirculated at a flow rate of ⅓ less than for 3 segments. The second segment is then dosed and the entire process repeated until all 3 segments have been dosed and aliquots of perfusate collected at timed intervals up to about one hour to about two hours post-dosing for each time zero.

Biopsies

Biopsies are preferably taken pre-dosing and at the termination of the perfusion and flash-frozen in liquid nitrogen at the point of collection prior to the homogenization. The biopsies can be subjected to histopathology and phenotyping for marker enzymes and other proteins.

Controls

Preferred controls include, but are not limited to, aliquots of perfusate and plasma collected pre-dosing, and, if possible, intestinal homogenates collected from a separate organ. Controls are preferably stored at about −80° C.

Analysis

Absorption of the test substance is determined by analyzing its rate of absorption from the intestinal lumen into the recirculating perfusate with time and comparing the rate with that of the internal standards. The raw data is generally in pmoles/ml, total pmoles and/or percent dose and includes the percent fraction for all absorbed compounds and the mass balance of labeled test substance in the perfusate, plasma, intestinal contents and intestinal wall. If radiolabeled compounds and standards are used, then total radioactivity measurements can be taken, and, if desired, HPLC profiling of the labeled test compound can be performed.

During perfusion, physiological parameters are monitored, such as arterial pressures and flows, organ core temperature, blood pH, active peristalsis and arterial and venous $PO_2$ and $PCO_2$; blood biochemistry parameters, such as electrolyte balance including, but not limited to, concentrations of potassium (mM), sodium (mM), chloride (mM), calcium (mM), albumin (g/dl), ALP (alkaline phosphatase) (U/l), ALT (alanine transaminase) (U/l), amylase (U/l), AST (aspartate transaminase) (U/l), GGT (gamma glutamyl transferase) (U/l), Cal (mg/dl) and BUN (blood urea nitrogen) (mg/dl); biomarkers, such as, glucose (mg/dl) utilization and lactate (mM) production; absorption of internal standards, such as 3H-mannitol (target concentration about 100 µCi; target dose about 20 µM), antipyrine (target dose about 20 µM), terbutaline (target dose about 20 µM), dextran (about 10 to about 70 kD) and/or other labeled or unlabeled standards; and presence and characteristics of the test compound and/or metabolites.

Perfused Liver Protocol

Currently, attempts to predict human liver metabolism are performed with data from in vitro preparations, i.e., tissue slices, isolated hepatocytes, S9 fractions or microsomes. Although these studies are important, they sometimes: (a) do not mimic metabolism in the whole liver; (b) identify potential rather than actual metabolism; and (c) give no measure of subsequent partitioning of metabolites between blood and bile, and thus the exposure of extra-hepatic organs and tissues to the byproducts of liver metabolism.

In isolated vascular perfused human liver studies, these shortcomings may be avoided. Instead, test substances and validation standards may be delivered via matched blood-based perfusate at physiological flow rates to a stable, viable hepatic organ or tissue with normal biliary secretory mechanisms. Consequently, this model is ideally suited to determine the nature and extent of substance uptake, metabolism and clearance in the human liver, as well as biliary elimination, mass-balance and measurements of the subsequent partitioning of metabolites between blood and bile. In addition, specific metabolites may be characterized in separate studies.

Exemplary Perfusion Conditions

Approximately five to six liters of perfusate are used per analysis. Fresh perfusate containing human erythrocytes (previously washed and centrifuged) is suspended in buffer containing 6% human serum albumin (at about room temperature, about 15 to about 20% v/v, pH about 7.4). If the test substance is known to bind to α-1-glycoprotein, then 4% human serum albumin is used instead of 6%, plus 2% α-1-glycoprotein. The perfusate is then passed through a Pall 40 micron blood transfusion filter, followed by a leukocyte-removing filter, approximately 15 N.I.H. units/ml of heparin are added and the pH adjusted, if necessary, to approximately 7.4. The perfusate is preferably stored at room temperature until added to the perfusion apparatus. An aliquot of the surplus perfusate, such as approximately 50 ml, may be centrifuged (approximately 1500 g for approximately 10 minutes at approximately 4° C.) to separate the plasma and blood cells. This plasma may be frozen at approximately −20° C. or lower for use as blanks in the analysis.

Throughout the perfusion, the flow, pressure and temperature are recorded in the portal vein and the hepatic artery. The $PO_2/PCO_2$ is measured at approximately 15 minute intervals in the inlets via the hepatic artery and portal vein and in the outlet via the vena cava. Each liver is allowed an equilibration period of about 45 to about 60 minutes and bile is collected in pre-weighed containers. Only satisfactory preparations, in terms of perfusate flow and pressure and bile flow are dosed with test substances.

Supplementary bile salts are added initially to the perfusate and then throughout the perfusion period. Bile salts include, but are not limited to, about 1 gram of sodium glycocholate hydrate (Sigma G7132), about 0.5 gram sodium glycodeoxycholate (Sigma G9910) and sodium glychochenodeoxycholate (Sigma G0795) dissolved in 25% hydroxypropyl beta cyclodextrin (HPPCD), wherein the total mass of bile salt in the HPPCD solution is 20 g. About 1 gram of bile salt HPPCD solution per liter of perfusate is preferred initially, followed by about 1 gram of solution into the perfusate at 1, 2, 3, 4 and 5 hours. Thus, the perfusate will be comprised of washed matched human erythrocytes suspended in human plasma supplemented with bile salts.

Perfused Liver Samples

An isolated human liver is removed from hypothermic storage and, if possible, the hepatic artery, portal vein and vena cava are cannulated. The liver is then flushed at about room temperature with about one liter to about two liters of cold buffer, such as Krebs-Ringer bicarbonate buffer (pH approximately 7.4), under gravity, for about 10 to about 15 minutes, to remove the transport/storage medium.

About 1.5 liters of fresh perfusate containing human erythrocytes (previously washed) suspended in buffer containing 4% or 6% human serum albumin, as described above, at about room temperature, about 15 to about 20% v/v, pH about 7.4, are then pumped at approximately 20 ml/min. into the hepatic artery and portal vein and allowed to recirculate for about 45 to about 60 minutes in an equilibration phase.

After approximately 1 liter has run to waste, about two liters of fresh perfusate are recirculated within the perfusion apparatus. The temperature of the perfusate is raised to about 37° C. and perfusion flow rates are increased to target flow rates, e.g., about 200 to about 300 ml/min. through the hepatic artery and about 400 to about 800 ml/min., preferably about 600 ml/min., through the portal vein for about 10 to about 15 minutes in a stabilization phase.

Dosing and Sample Collection

The solubility and stability of the test substance are preferably confirmed prior to the perfusion study as described above. Once the perfusion preparations are stable with respect to perfusate flow and pressure, the test substance is added to the recirculating perfusate. Preferred acceptance criteria for normothermic perfusion of human liver prior to dosing with a test substance are:

| Perfusion & Physiological Parameters | |
| --- | --- |
| Arterial pressure (mmHg) | 40-60 |
| Arterial flow (ml/min.) | 200-300 |
| Portal pressure (mmHg) | 15-22 |
| Portal flow (ml/min.) | 600-800 |
| Venous PO$_2$ | >26 |
| Arterial PO$_2$ | >120 |
| PH | 7.3 ± 0.2 |
| Temperature (° C.) | 36.5 ± 2 |
| PCV (% cells) | 15-20 |

The dosing vehicle is preferably aqueous, or in the case of compounds with poor aqueous solubility, is DMSO at a final concentration of about 0.1% v/v in perfusate. The preferred dosing regime comprises adding about 50 mg of, preferably, labeled, such as radiolabeled, test compound or a mixture of non-labeled and labeled, such as radiolabeled, test compounds, in DMSO as an infusion into the perfusate over a period of time (median Tmax=about 1 hour). If radiolabels are used, the target radioactive dose is preferably about 100 µCi per liver.

Each dosing solution is preferably put into a pre-weighed syringe with an attached cannula and the syringe is reweighed. The contents of the syringe are expelled as a pulse dose into the perfusate. The test substance is added at designated "time zero" and the liver perfused for about 240 minutes. A standard, such as tetra-BSP (about 20 µM), is added at the end of the about 240 minutes and the liver is perfused for about 120 minutes more. The liver is perfused for about six hours in total post-dosing. Perfusate samples (about 10 ml per sample) are collected, for example, at least two of the following times during perfusion: pre-dose and 5, 10, 15, 30, 45, 75, 105, 135, 165, 195, 225 and 239 minutes post-dose.

In addition, bile is continuously collected throughout the perfusion, for example, at least two of the following times: pre-dose and 30, 60, 90, 120, 150, 180, 210 and 240 minutes post-dose.

The liver is dosed with at least one positive control at about four hours after "time zero" and the perfusate sampled, for example, at least two of the following times: 245, 150, 255, 270, 285, 300, 330 and 360 minutes past time zero.

From each about 10 ml sample, about 1 milliliter is retained as whole perfusate and the remaining about 9 milliliters centrifuged and the plasma supernatant divided into four approximately equal aliquots. The supernatants and bile samples can be stored at about −80° C. until analyzed for dosed test substance and any metabolites. Following sampling of each about 10 ml aliquot, about 10 ml of control perfusate (perfusate without the test substance) is added to the perfusion system to maintain a constant volume.

At perfusion termination, all the remaining perfusate and apparatus washings are collected for mass-balance analysis and/or metabolite profiling, if desired (in perfusate/plasma). The gall bladder, if not dissected from the liver prior to the perfusion, can be homogenized and assayed for total radioactivity, assuming the test substance is radiolabeled.

After the tissue is collected, the perfusion apparatus is preferably rinsed with saline and, at the end of the perfusion, with water and alcohol. A sample of each rinse is preferably retained for analysis. In addition, the dosing syringe and cannula are reweighed after dosing and washed with water and methanol. The syringe/cannula washing is assayed for radioactivity, if applicable, or other label, if applicable. The test substance dose administered is calculated by subtracting the syringe washings from the total amount of radioactivity, for example, taken-up into the syringe/cannula.

Biopsies

Biopsies are preferably taken pre-dose and at 360 minutes post-dose and flash-frozen in liquid nitrogen at the point of collection. The remainder of the liver is homogenized at the end of the perfusion. The biopsies can be subjected to histopathology and phenotyping for marker enzymes and other proteins.

Controls

Preferred control samples include, but are not limited to, aliquots of bile, perfusate and plasma collected pre-dose, and, if possible, liver homogenates collected from a separate organ. All samples are preferably stored at about −80° C.

Analysis

If radiolabeled substances and standards are used, then total radioactivity measurements can be taken, and, if desired, extraction and HPLC profiling of the labeled test substance and/or metabolites can be performed. In addition, possible structural identification may be performed on metabolites and extraction and analysis of the standard, such as tetra-BSP and its glutathione conjugates in plasma and bile, can be conducted.

During perfusion, physiological parameters may be monitored, such as arterial pressure and flow, organ core temperature, blood pH and arterial and venous PO$_2$ and PCO$_2$; blood biochemistry parameters such as electrolytes including, but not limited to, potassium (mM), sodium (mM), chloride (mM), calcium (mM), albumin (g/dl), ALP (U/l), ALT (U/l), amylase (U/l), AST (U/l), GGT (U/l), Cal (mg/dl), bilirubin (U/l), and BUN (mg/dl); biomarkers such as glucose (mg/dl) utilization and lactate (mM) production; absorption of standards such as 3H-mannitol, antipyrine, propanalol, atenolol, bromosulphophthalein (tetra-BSP), 1-naphthol, 7-ethoxycoumarin, terbutaline and/or other labeled or unlabeled standards; and presence and characteristics of the test substance and/or metabolite(s) in bile, perfusate and liver.

Perfused Kidney Protocol

Processes of particular relevance to assessing the fates and effects of substances on kidneys include, but are not limited to: (a) renal clearance, plasma clearance, and glomerular filtration rate—urine is the principle route of substance elimination and the kidneys are a major site for substance interactions; (b) metabolism—the kidneys have significant metabolizing activities such as determining percent tubular reabsorption or active secretion; and (c) distribution—the partitioning of metabolites formed in the kidneys between blood and urine can dictate the subsequent exposure of other organs to pharmacologically active or toxic metabolites.

As with all human organs, the validation process for isolated perfused human kidneys (IPHK) is designed for both hypothermic preservation perfusion after excision of the kidney from the donor and normothermic physiological perfusion for substance testing.

Optionally, prior to testing using IPHK, as much as possible is known about the history of each kidney in the test and, more importantly, its current condition compared with a database of hundreds of kidneys that were successfully transplanted and those that were not. This is the mechanism by which kidneys are accepted for drug research and the rationale for each decision is recorded. However, in accordance with the present disclosure, the kidneys need not be in the same condition as they would need to be in for transplantation. Thus, e.g., organs from older donors than would be acceptable for transplantation (e.g., older than 56 years) and from non-beating-heart donors, as well as diseased and injured organs, may be used.

Perfusion Conditions

Donated kidneys are transferred to hypothermic storage as soon as possible after collection and perfused with a buffer, such as KPS-1® buffer (Organ Recovery Systems, Inc., Des Plaines, Ill.), at about 6 to about 8° C. for a minimum of about 4 hours.

The kidney(s) is then flushed with about 1 liter of fresh perfusate and the temperature of the perfusate effluent raised to about 37° C. When the kidney(s) is stable with respect to perfusion pressure and flow and urine formation, the first perfusate is replaced with about 1.5 liters of fresh perfusate.

Dosing and Sample Collection

Preferred acceptance criteria for normothermic perfusion of human kidneys prior to dosing with a test substance are:

| Perfusion & Physiological Parameters | |
| --- | --- |
| Perfusion pressure (mmHg) | 40-80 |
| Perfusate flow rate (ml/min.) | 250-450 |
| PH | 7.4 ± 0.3 |
| Temperature (° C.) | 36.5 ± 2 |
| Glomerular filtration rate (GFR) (ml/min.) | 20-80 |
| Venous $PO_2/PCO_2$ | 20-50/5-30 |
| Arterial $PO_2/PCO_2$ | 120-140/5-30 |
| PCV (% cells) | 16-22 |

The test substance and internal standards are dosed directly into the perfusate and aliquots of perfusate (about 3 ml to about 5 ml) are taken about every 15 minutes and urine collected batchwise about every 15 minutes for about 2 hours. Each perfusate sample is subdivided into four approximately equal aliquots. Two aliquots are retained for analysis and the other two centrifuged and the plasma removed and stored frozen at about −70° C. for additional analysis if required. Urine samples are collected into tarred tubes, weighed and frozen at about −70° C. for subsequent analysis of, for example, test substances and metabolites.

After the test substance has been administered to an IPHK for sufficient time, for example, about 60 minutes, exogenous positive controls can be added to the circulating perfusate to validate those critical processes not covered by endogenous compounds, i.e., the internal standards. These additional, preferably labeled, controls include, but are not limited to, p-amino hippuric acid (for assessing tubular secretion) and a glutathione conjugate (for assessing the integrity of the mercapturic acid pathway).

Perfusate and urine samples are collected about every 30 minutes for a further about 2 hours after dosing the positive controls and are retained for analysis, which includes, but is not limited to, measuring physiological parameters; measuring blood chemistry parameters, such as potassium (mM), sodium (mM), chloride (mM), calcium (mM), glucose (mg/dl), lactate (mM), albumin (g/dl), ALP (U/l), ALT (U/l), amylase (U/l), VAG (U/l), AST (U/l), 2-GST (glutathione S-transferase) (U/l), creatinine (mg/dl) and urinary excretions (U/l); measuring test substances and/or metabolites in urine, perfusate and kidney; and measuring parameters of urine biochemistry, such as N-acetylglucosaminidase, glutathione S-transferase, and proteins and peptides.

Perfused Human Lung Protocol

The isolated perfused human lung preparation (IPHLung) is a versatile system for studying lung-specific substance-related effects including, but not limited to, assessing, e.g., quantitating ventilatory function, substance absorption via the airways, substance uptake in the blood, substance metabolism, clearance and retention, extent of edema, substance toxicity and drug interactions, as well as assessing physiologic function of the lungs by inducing bronchoconstriction/dilatation with histamine/salbutamol, or other standard, using nebulized delivery.

Moreover, perfusion studies overcome numerous problems of in vitro lung studies, including, but not limited to, allowing for the over 40 cell types in the lung, many of which cannot be isolated and many of which change their phenotype when cultured.

Perfusion Conditions

Preferably, a pair of respiring lungs is flushed free of donor blood with about 2 liters of buffer, such as Krebs-Ringer buffer, at about 6 to about 8° C. at about 12 to about 18 ml/min. The lungs are then perfused via the pulmonary artery with fresh perfusate with a pressure of less than about 18 mmHg and the flow continuously recorded. The effluent from the pulmonary veins can be recirculated (except under first-pass conditions). About two liters of perfusate are used for the perfusion study.

Preferred biomarkers are enzymatic, including, but not limited to, angiotensin converting enzyme. Preferred standards include, but are not limited to, about 1 mg/ml salbutamol or other bronchodilator (dose of about 150 μg), about 1 mg/ml ipatropium (dose of about 150 μg) and polyamines.

Dosing and Sample Collection

Preferred acceptance criteria for normothermic perfusion of human lungs prior to dosing with a test substance are:

| Perfusion & Physiological Parameters | |
| --- | --- |
| Perfusion pressure (mmHg) | ≤18 |
| Perfusate flow rate (ml/min.) | 1000-3000 |
| pH | 7.4 ± 0.3 |
| Temperature (° C.) | 37.0 ± 1 |
| Airflow (l/min.) | at least 66 |
| Tidal volume (ml) | 500-1000 |
| Lung Function Tests | @ about 10-20 second intervals |

Pre-dose and at other sample times, perfusate samples are taken and blood chemistry is assessed in terms of, for example, pH, $pCO_2$, lactate and inorganic ions. In addition, samples are taken at the same times to assess release of angiotensin converting enzyme and other enzymes.

After dosing of the test substance, via the airway using a nebulizer or into the perfusate, at a concentration of about 0.3 to about 1.0 mg/ml (dosage of about 45 to about 150 μg) (referred to as "time zero"), aliquots (preferably about 3 to about 5 ml) of perfusate are removed pre-dose and at least two of the following times: 5, 10, 15, 30, 45, 60, 90 and 120 minutes post-dose for absorption studies, for example. About 1 ml of each aliquot is retained for blood chemistry/biochemistry and hematocrit measurements. A portion of the remaining aliquot is set aside (about 1 ml whole perfusate) and the remainder is centrifuged and the resulting cell-free supernatant further divided into aliquots, which are flash frozen in liquid nitrogen at the point of collection.

After about 120 minutes post-dose, the perfusate is replaced with fresh perfusate, which is circulated for about 30 minutes. Perfusate samples (about 3 to about 5 ml aliquots) are taken at, for example, 5, 10, 15 and 30 minutes from the beginning of the fresh perfusate circulation. About 1 ml of each aliquot is retained for blood chemistry/biochemistry and hematocrit measurements. A portion of the remaining aliquot is set aside (about 1 ml whole perfusate) and the remainder is centrifuged and the resulting cell-free supernatant further divided into aliquots, which are flash frozen in liquid nitrogen at the point of collection.

At the end of the 30 minutes, metabolic markers are added to the perfusate and the perfusate is again sampled at, for example, 5, 15, 30 and 60 minutes (to the end of the perfusion and/or at other time points, if feasible) after metabolic marker addition in about 3 to about 5 ml aliquots, which are subsequently frozen for later analysis of test compounds and metabolites. About 1 ml samples of plasma are also taken at, for example, 5, 15, 30 and 60 minutes (and other time points as feasible) after metabolic marker addition for polyamine uptake determination. Markers include, but are not limited to, probes added to the perfusate, ethoxycoumarin (CYP1A) at a dose of about 20 µM, and 1-naphthol (glucuronidation and sulfation) at a dose of about 10 µM.

At about three hours and 30 minutes from time zero, histamine, or other bronchoconstrictor or vasodilator, is added to the perfusate at a concentration of about $10^{-5}$ M to about $10^{-6}$ M for a pharmacology evaluation. About ten minutes later, bronchoconstriction is assessed. If evidence of bronchoconstriction is not found, then histamine is again added, but at an increased concentration of about $10^{-6}$ M to about $10^{-5}$ M, respectively. Increased concentrations of histamine are added to the perfusate every ten minutes until evidence of bronchoconstriction is apparent at which time inhalation of a control, such as salbutamol, is initiated at a dosage of 2×150 µg from 1 mg/ml stock solution. Preferably dosing is performed using a ProDose device with a 150 µl disk. The presence of bronchodilation is determined over about 15 minutes. Papaverine or other vasodilator may then be added to the perfusate at a concentration of about $10^{-7}$ M and the extent of bronchodilation determined.

Biopsies

Histology studies can be performed on each lung using a container, such as a 500 ml plastic screw-top container, filled with neutral buffered formalin, for example. The lung lobes are removed with the entire length of the bronchus, avoiding damage to the parenchymal tissue. A ligature is loosely placed around the bronchus. The bronchus can be held with forceps and a syringe used to slowly insufflate the entire lung lobe with formalin. Insufflation is discontinued after the lobe is expanded 75%. The bronchus is ligated and the lobes are placed in the formalin. The date and time of this initial fixation are noted.

Hepatotoxicity

There are five commonly used whole cell preparations for the study of hepatic functions and toxicity: primary hepatocytes, hepatocytes in culture, liver slices, perfused livers and livers in vivo. Each of these methods has advantages and disadvantages that should be taken into account when designing experiments to determine the fates and effects of substances in vivo. In practice this has proven to be a difficult standard to meet. For example, references to major advantages attributed to the use of isolated hepatocytes in drug research always include "convenience" and the "large quantity" of data generated from a single liver. However, when "quality" of data is paramount, e.g., when making drug development decisions, this in vitro model suffers from a loss of lobular architecture, regional distribution of enzymes is disrupted, the cells have diminished activity of many enzymes and important non-parenchymal cells are absent. Similarly, in cultured hepatocytes, many enzyme systems revert to fetal states and cytochrome P450 content declines limiting their use in toxicity and drug metabolism studies. However, these methods remain widely used in the absence of alternatives.

In contrast to primary or cultured hepatocytes, liver slices retain lobular architecture, however cells in this form leak potassium and most importantly do not produce bile, a major route for clearing potential toxins (endogenous and exogenous) from the liver.

Perfused liver systems simulate in vivo conditions more than any of the techniques above. Normal hepatic architecture, microcirculation and bile production are maintained. Compounds, free and protein-bound, are delivered to all cell types via the blood (cells and plasma) at the same flow rates and perfusion pressures operating in vivo. Moreover, in assessing substances for hepatotoxicity, the fact that the numerous cell types in perfused livers are less compromised, results in fewer false positives and false negatives and better pharmacokinetic/toxicity correlations.

A. Perfusion Conditions

Human-derived livers are perfused as described above. Test substances are added to the perfusate as (a) a pulse dose, (b) repeated pulse doses, (c) constant infusion or (d) rising plasma concentrations. Perfusate and bile samples are collected every about 15-30 minutes over about 4-8 hours and analyzed for markers of hepatic/biliary damage in addition to substance/metabolite concentrations. In one embodiment, liver biopsies are taken every hour and flash frozen in liquid nitrogen at the point of collection as described above.

B. Markers of Toxicity and Positive Controls

| Target Syndrome | Method of Diagnosis & Histochemistry |
|---|---|
| Fatty liver formation | Inhibition of carrier protein synthesis |
| Cholestasis | Biliary excretion |
| Necrosis | Proteomics |
| Apoptosis | Proteomics, imaging |
| Ischemia/Reperfusion Injury | Protein adducts |
| Genotoxicity | DNA-adducts |
| Enhanced Portal Pressure | Direct |
| Induction/Repression | Microarrays |
| Detoxification Pathways | Activation/Inhibition |

Collectively, this battery of assays records the effects of substances and/or metabolites, at relevant concentrations in blood, on some of the key liver functions including: transport processes in and out of the liver, transcription-translation-post translational modification and exocytosis of proteins and conjugated proteins, cytokine production, stimulation of apoptosis or necrosis, free radical generation, DNA-adduct formation and induction or inhibition of detoxification pathways.

Nephrotoxicity

As a vital organ, the kidney performs many unique functions that can be monitored for evidence of impairment when exposed to certain substances. These functions include: regulation of the body's fluid volume (a major contributor to the control of blood pressure); regulating the pH of the body in concert with lungs through the excretion of fixed, non volatile acids and the conservation of bases; excretion of waste products and the conservation of critical body constituents, e.g., electrolytes, substrates etc.; detoxification of certain substances; synthesis and release of hormones, such as rennin and erythropoetin; and the conversion of vitamin $D_3$ to the 1,2-dihydroxy form. To carry out these functions, the integration of many physiological and biochemical actions of the kidney is required.

A. Perfusion Conditions

Human-derived kidneys are subjected to hypothermic perfusion, flushed and stabilized with perfusate at about 37° C. and perfused with about 1 to about 1.5 liters of fresh perfusate as described above.

Test substances are added to the perfusate as (a) a pulse dose, (b) repeated pulse doses, (c) constant infusion or (d) rising plasma concentrations. Perfusate and urine samples are collected about every 15-30 minutes over about 2-4 hours during perfusion and analyzed for markers of renal damage in addition to substance/metabolite concentrations.

C. Markers of Toxicity and Positive Controls

| Target Syndrome | Positive Controls | Method of Diagnosis |
| --- | --- | --- |
| Acute renal failure | Gentamycin Cisplatin | Proteomics |
| Pre renal azotaemia due to impaired perfusion | ACE inhibitors Cyclosporins | Renal haemodynamics |
| Acute intestinal nephritis | Allopurinol Sulphonamides | Markers of inflammation |
| Obstructive nephropathy | Methotrexate Acyclovir | Urine flow GFR |

Cardiac Toxicity

A. Perfusion Conditions

After preservation, isolated human hearts are removed from cold storage and perfused, in the standard Langendorff format with a buffer comprising washed matched human erythrocytes (about 15 to about 20% v/v) and human serum albumin (about 4% w/v) at a pH of about 7.3±2 and a temperature of about 37° C. In one embodiment, human serum albumin may be replaced with human plasma.

$PO_2$ (about 150 to about 250 mmHg) and $PCO_2$ (about 25 to about 35 mmHg) are maintained and electrolyte concentrations adjusted to normal values in blood. Once the organ is stable with respect to perfusate pressure and flow, heart rate and developed left ventricular pressure (DLVP) (dP/dt) and a pre-dose sample has been removed, test substances are added to the perfusate as (a) a pulse dose, (b) repeated pulse doses, (c) constant infusion or (d) rising dose infusion. Blood chemistry/biochemistry markers, including, but not limited to, electrolytes, glucose, $PO_2$ A-V difference, $PCO_2$ A-V difference, troponin-1 and albumin conjugates, are measured.

B. Markers of Toxicity and Positive Controls

| Target Syndrome | Method of Diagnosis |
| --- | --- |
| Langendorff properties | Pressure Flow Heart rate |
| Re-animation interventions | Defibrillation Pacing Isotopes |
| Work Capacity | dP/dt |
| Diastolic | End diastolic pressure - volume ratio |
| Endothelial function | Coronary flow reserve |
| Disruption of cellular function | Proteomics |
| Apoptosis | Caspase 3 |
| Necrosis | Troponin-1 |
| Ischemia | Albumin adducts |

Identification of Hormone Disrupters

There is an urgent need for validated in vivo and in vitro screening assays to test manufactured chemicals and drugs for hormone disruption activities. Hitherto, many of the screens available use non-mammalian vertebrates and invertebrates, which may not be representative of events in mammals including humans. The perfusion of human endocrine glands, utilizing adrenal, thymus, pancreas, thyroid and reproductive organs, with blood ex vivo, provides a test system that is relevant to humans. An exemplary protocol involves the blood perfusion of the endocrine glands via the normal vasculature and collection of the venous effluent by cannulation of the appropriate veins. The up-take of naturally occurring hormones by the glands and the subsequent release of endogenously produced hormones by the glands are both measured in the absence (controls) and presence (tests) of potential hormone disruptors added to the perfusate at concentrations which are clinically and/or environmentally relevant. Thus the activity of potential chemical substances for hormone disruption may be evaluated.

In the practice of the methods of this invention, devices and apparatus for perfusing organs and tissues for transplant can be used, as disclosed in co-owned U.S. Pat. No. 6,673,594 and U.S. Published Patent Application No. 2004/0224298, each of which is expressly incorporated by reference in its entirety herein. However, one of ordinary skill in the art will recognize that there are differences in the way organs and tissues are used according to the inventive methods and the way organs and tissues are maintained by perfusion for organ transplantation.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention and that modifications or alternatives equivalent thereto are within the spirit and scope of the invention.

What is claimed is:

1. A method of testing the toxicity of a substance, comprising:

passing a perfusate comprising the substance under normothermic conditions and physiological oxygenation, osmolality, electrolyte balance and pH conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate under normothermic conditions and physiological oxygenation, osmolality, electrolyte balance and pH conditions that does not contain the substance through the at least one donated human organ or tissue before and/or after passing the at least one donated human organ or tissue with the perfusate comprising the substance, wherein the at least one donated human organ or tissue acts as its own control, the perfusate that does not contain the substance comprises the positive and negative controls, and the perfusate that does not contain the substance further comprises about 15 to about 20% (v/v) matched human erythrocytes, about 2 to about 6% human serum albumin, N-acetylcysteine, and adenosine monophosphate (AMP);

collecting data derived from the perfused organ or tissue, wherein collecting data derived from the perfused organ or tissue comprises:

assaying an effluent from the perfused organ or tissue, and monitoring one or more parameters selected from the group consisting of cell death, apoptosis, genetic mutation, changes in gene expression, biochemical inhibition, reduction in metabolism, induction and oxidative damage, hormone disruption, and bodily chemical disruption; and analyzing the data to assess the toxicity of the substance, wherein the substance is selected from the group consisting of agricultural products, industrial products, building materials, tobacco products, cleaning products and cosmetics; wherein said at least one metabolically active ex vivo donated human organ or tissue is a glandular organ or tissue.

2. The method of claim 1, wherein the data are collected by electrophysiological testing, medical diagnostic imaging, spectroscopic testing, microdialysis, solid state tissue probe testing or a combination thereof.

3. The method of claim 1, wherein the substance is selected from the group consisting of industrial products, building materials and cleaning products.

4. The method of claim 3, wherein the cleaning products are selected from the group consisting of detergents, bleaches, soaps, shampoos and conditioners.

5. The method of claim 1, wherein the substance is selected from the group consisting of tobacco products and cosmetics.

6. A method of testing the toxicity of a substance, comprising:

passing a perfusate comprising the substance under normothermic conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the donated human organ or tissue before and/or after perfusing the donated human organ or tissue with the perfusate comprising the substance, wherein the donated human organ or tissue acts as its own control, the perfusate that does not contain the substance comprises the positive and negative controls, the perfusate that does not contain the substance further comprises about 15 to about 20% (v/v) matched human erythrocytes, about 2 to about 6% human serum albumin, N-acetylcysteine, and adenosine monophosphate (AMP); and but for the presence of the substance, the perfusate comprising the substance is compositionally the same as the perfusate that does not contain the substance;

collecting data derived from the perfused organ or tissue, wherein collecting data derived from the perfused organ or tissue comprises:

assaying an effluent from the perfused organ or tissue, and monitoring one or more parameters selected from the group consisting of cell death, apoptosis, genetic mutation, changes in gene expression, biochemical inhibition, reduction in metabolism, induction and oxidative damage, hormone disruption, and bodily chemical disruption; and analyzing the data to assess the toxicity of the substance, wherein the at least one metabolically active ex vivo donated human organ or tissue is an intact organ or tissue, and data are used to analyze at least one of the following: hormone level, target cell-receptor mediation, glandular secretion function, hormone function, organ function and a combination thereof; wherein the substance is selected from the group consisting of agricultural products, industrial products, building materials, tobacco products, cleaning products and cosmetics; wherein said at least one metabolically active ex vivo donated human organ or tissue is a glandular organ or tissue.

7. A method of testing the toxicity of a substance, comprising:

passing a perfusate comprising the substance under normothermic conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the donated human organ or tissue before and/or after perfusing the donated human organ or tissue with the perfusate comprising the substance, wherein the donated human organ or tissue acts as its own control, and the perfusate that does not contain the substance comprises the positive and negative controls, wherein the perfusate that does not contain the substance further comprises about 15 to about 20% (v/v) matched human erythrocytes, about 2 to about 6% human serum albumin, N-acetylcysteine, and adenosine monophosphate (AMP);

collecting data derived from the perfused organ or tissue, wherein collecting data derived from the perfused organ or tissue comprises assaying an effluent from the perfused organ or tissue, and analyzing the data to assess the toxicity of the substance, wherein the organ or tissue is selected from the group consisting of endocrine glands and exocrine glands, and analyzing the data comprises determining a concentration of the substance at which the secretion ability of said glands decreases, increases or is otherwise altered; wherein the substance is selected from the group consisting of agricultural products, industrial products, building materials, tobacco products, cleaning products and cosmetics.

8. A method of testing the toxicity of a substance, comprising:

passing a perfusate comprising the substance under normothermic conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the donated human organ or tissue before and/or after perfusing the donated human organ or tissue with the perfusate comprising the substance, wherein the donated human organ or tissue acts as its own control, and the perfusate that does not contain the substance comprises the positive and negative controls, wherein the perfusate that does not contain the substance further comprises about 15 to about 20% (v/v) matched human erythrocytes, about 2 to about 6% human serum albumin, N-acetylcysteine, and adenosine monophosphate (AMP);

collecting data derived from the perfused organ or tissue, wherein collecting data derived from the perfused organ or tissue comprises assaying an effluent from the perfused organ or tissue; and analyzing the data to assess the toxicity of the substance, wherein the organ or tissue is an organ selected from the group consisting of pancreas, thymus, male reproductive organs, female reproductive organs, thyroid gland and adrenal gland, and analyzing the data comprises determining the concentration of substance at which the rate of production of secretory products or concentration of secretory products of the organ decreases, increases or is otherwise altered; wherein the substance is selected from the group consisting of agricultural products, industrial products, building materials, tobacco products, cleaning products and cosmetics.

9. A method of testing the toxicity of a substance, comprising:

passing a perfusate comprising the substance under normothermic conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the donated human organ or tissue before and/or after perfusing the donated human organ or tissue with the perfusate comprising the substance, wherein the donated human organ or tissue acts as its own control, and the perfusate that does not contain the substance comprises the positive and negative controls, wherein the perfusate that does not contain the substance further comprises about 15 to about 20% (v/v) matched human erythrocytes, about 2 to about 6% human serum albumin, N-acetylcysteine, and adenosine monophosphate (AMP);

collecting data derived from the perfused organ, or tissue, wherein collecting data derived from the perfused organ or tissue comprises assaying an effluent from the perfused organ or tissue;

analyzing the data to assess the toxicity of the substance; and quantifying a functional state of the donated human organ or tissue that was injured or diseased before donation, wherein the passing comprises perfusing the organ or tissue with a first perfusate that does not contain the substance, followed by perfusing the organ or tissue with a second perfusate that contains the substance; wherein the substance is selected from the group consisting of agricultural products, industrial products, building materials, tobacco products, cleaning products and cosmetics; wherein said at least one metabolically active ex vivo donated human organ or tissue is a glandular organ or tissue.

10. The method of claim 9, wherein the organ or tissue is an entire organ or tissue and has been injured by mechanical injury.

11. The method of claim 9, wherein the organ or tissue is an entire organ or tissue and diseased with a disease that the substance comprised in the perfusate is intended to treat.

12. A method of testing the toxicity of a substance, comprising:

passing a perfusate comprising the substance under normothermic conditions through at least one metabolically active ex vivo donated human organ or tissue that was injured or diseased before donation, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the donated human organ or tissue before and/or after perfusing the donated human organ or tissue with the perfusate comprising the substance, wherein the donated human organ or tissue acts as its own control, and the perfusate that does not contain the substance comprises the positive and negative controls, wherein the perfusate that does not contain the substance further comprises about 15 to about 20% (v/v) matched human erythrocytes, about 2 to about 6% human serum albumin, N-acetylcysteine, and adenosine monophosphate (AMP);

collecting data derived from the perfused organ or tissue, wherein collecting data derived from the perfused organ or tissue comprises assaying an effluent from the perfused organ or tissue;

analyzing the data to assess the toxicity of the substance;

quantifying a functional state of the donated human organ or tissue that was injured or diseased before donation with respect to a hormone level, wherein the data are analyzed to assess whether the hormone level is unaltered or is increased, decreased or otherwise altered in response to passing the perfusate comprising the substance under normothermic conditions through said at least one metabolically active ex vivo donated human organ or tissue; wherein the substance is selected from the group consisting of agricultural products, industrial products, building materials, tobacco products, cleaning products and cosmetics; wherein said at least one metabolically active ex vivo donated human organ or tissue is a glandular organ or tissue.

13. The method of claim 12, wherein the substance is selected from the group consisting of industrial products, building materials, tobacco products and cleaning products.

14. A method of testing the toxicity of a substance, comprising:

passing a perfusate comprising the substance under normothermic conditions through at least one metabolically active ex vivo donated human endocrine gland or endocrine gland tissue under normothermic conditions, wherein perfusate comprising the substance further comprises about 15 to about 20% (v/v) matched human erythrocytes, about 2 to about 6% human serum albumin, N-acetylcysteine, and adenosine monophosphate (AMP);

passing a perfusate that does not contain the substance through the human endocrine gland or endocrine gland tissue before and/or after perfusing the human endocrine gland or endocrine gland tissue with the perfusate comprising the substance, wherein the human endocrine gland or endocrine gland tissue acts as its own control, and the perfusate that does not contain the substance comprises the positive and negative controls, wherein the perfusate that does not contain the substance further comprises about 15 to about 20% (v/v) matched human erythrocytes, about 2 to about 6% human, serum albumin, N-acetylcysteine, and adenosine monophosphate (AMP);

collecting data derived from the perfused gland or gland tissue, wherein collecting data derived from the perfused gland or gland tissue comprises assaying an effluent from the perfused gland or gland tissue;

quantifying a functional state of the at least one metabolically active ex vivo donated human endocrine gland or endocrine gland tissue with respect to hormone uptake or production; and analyzing the data to assess effects of the substance on the hormone uptake or production by said gland or gland tissue; wherein the substance is selected from the group consisting of agricultural products, industrial products, building materials, tobacco products, cleaning products and cosmetics.

15. The method of claim 14, wherein the data are collected by electrophysiological testing, medical diagnostic imaging, spectroscopic testing, microdialysis, solid state tissue probe testing or a combination thereof.

16. The method of claim 14, wherein the gland is selected from the group consisting of pancreas, thymus, male reproductive organs, female reproductive organs, thyroid gland and adrenal gland.

17. The method of claim 14, wherein the gland or gland tissue has been injured by prolonged warm ischemia.

18. The method of claim 14, wherein the gland or gland tissue has been injured by prolonged hypothermic storage.

19. The method of claim 14, wherein the gland or gland tissue has been injured by mechanical injury.

20. The method of claim 14, wherein the gland or gland tissue is diseased.

21. The method of claim 14, wherein the data are analyzed to assess whether a hormone level is unaltered or is increased, decreased or otherwise altered.

22. The method of claim 14, wherein the substance is selected from the group consisting of industrial products, building materials and cleaning products.

23. The method of claim 14, wherein the substance is selected from the group consisting of tobacco products and cosmetics.

* * * * *